United States Patent [19]

Haga et al.

[11] Patent Number: 5,757,479
[45] Date of Patent: May 26, 1998

[54] OPTICAL INSPECTION APPARATUS

[75] Inventors: Kazumi Haga; Motoshi Sakai; Satoshi Akiyama, all of Chofu, Japan

[73] Assignee: New Creation Co., Ltd., Japan

[21] Appl. No.: 625,136

[22] Filed: Apr. 1, 1996

[30] Foreign Application Priority Data

Mar. 31, 1995 [JP] Japan .................. 7-076310

[51] Int. Cl.⁶ .................................. G01N 21/00
[52] U.S. Cl. ............... 356/237; 356/236; 250/228
[58] Field of Search .......................... 356/237, 239, 356/236, 445, 446, 371; 250/228

[56] References Cited

U.S. PATENT DOCUMENTS

| | | | |
|---|---|---|---|
| 4,232,971 | 11/1980 | Suga | 356/236 |
| 4,583,860 | 4/1986 | Butner | 356/256 |
| 4,626,101 | 12/1986 | Ogawa et al. | 356/236 |
| 4,868,383 | 9/1989 | Kurtz et al. | 250/228 |
| 5,461,228 | 10/1995 | Kirkman et al. | 356/240 |
| 5,491,336 | 2/1996 | Concannon et al. | 356/236 |

*Primary Examiner*—Hoa Q. Pham
*Attorney, Agent, or Firm*—Evenson, McKeown, Edwards & Lenahan, P.L.L.C.

[57] ABSTRACT

There is provided an inspection apparatus which illuminates at least part of a sample with diffused light from a diffused light source and inspects the sample based on light reflected from the sample. An illuminating chamber is defined by a wall member. The wall member has an inner wall surface for reflecting diffused light from the diffused light source, a sample-inserting opening formed through the wall member for inserting the at least part of the sample into the illuminating chamber therethrough, and a sample-observing opening formed through the wall member for permitting light reflected from the at least part of the sample to be emitted out of the illuminating chamber. The sample is observed by the use of an object-side telecentric optical system having a lens system for collecting parallel light from the light emitted from the sample-observing opening, and an aperture stop arranged at or in the vicinity of a back focal point of the lens system.

12 Claims, 4 Drawing Sheets

OPTICAL INSPECTION APPARATUS

BACKGROUND OF THE INVENTION

1. Field of the Invention

This invention relates to an inspection apparatus for illuminating a sample, as an object of inspection, with light to thereby two-dimensionally or three-dimensionally check the surface of the sample, particularly the surface of a peripheral end of the sample, for a flaw (or a scratch), a foreign matter or the like.

2. Description of Related Art

Recently, semiconductor wafers with a larger diameter tend to be produced, and some of them have a diameter as large as 12 inches. In general, when the area of a semiconductor wafer becomes large, it is hardly to obtain a uniform thermal distribution on the semiconductor wafer. Therefore, if such a semiconductor wafer large in diameter has a flaw or a scratch at an end surface of the periphery thereof, an application of heat often makes the size of the flaw or a scratch large by the stress developed by nonuniform distribution of the heat. This can cause a discontinuity of a pattern of a semiconductor chip formed in the wafer, leading to a low yield of the semiconductor chip. Therefore, it is necessary to detect a flaw or a scratch, if any, of semiconductor chips, at an early stage of the manufacturing process, and determine a step of the manufacturing process at which the flaw is produced. For this purpose, an inspection apparatus is employed for checking the condition of a peripheral end of a semiconductor wafer for a flaw, a stain, a mark, a crack, etc. Such an inspection apparatus includes a type which irradiates a laser beam on a peripheral end of a semiconductor wafer and checks variation of analog information produced by a silicon photo diode sensitive to light reflected from the peripheral end of the semiconductor wafer, for a flaw, etc., and a type which irradiates diffused light on a peripheral end of a semiconductor wafer and checks light reflected therefrom by the use of a microscope.

According to these inspection apparatuses, out of light irradiated on to the peripheral end of a semiconductor wafer, only a portion reflected from a flat surface of the peripheral end without any flaw or the like enters the silicon photo diode or the microscope, while a portion reflected from a flaw or the like formed on the peripheral end of the semiconductor wafer is scattered and hence does not enter the silicon photo diode. This makes an area of the flaw or the like appear darker against its background, which makes it possible to detect the flaw or the like.

However, these inspection apparatuses suffer from the following problems: A peripheral end of a semiconductor wafer is curved with a predetermined curvature and projects outward in a radial direction like a mound. Therefore, to inspect such a peripheral end, particularly a peripheral end face, of the semiconductor wafer, if a laser beam or diffused light is irradiated as illuminating light thereon from a single direction, a shade of the semiconductor itself can be formed at a portion which does not face the illuminating light. This can result in an erroneous detection of a flaw or the like. If a portion or an area facing the illuminating light alone is inspected to eliminate this inconvenience, the size of the area which can be inspected at a time is reduced, which requires the semiconductor wafer to be moved many times to complete the inspection, resulting in a very long inspection time period.

Further, in the case of inspection by the use of the silicon photo diode, a laser beam is required to be irradiated in a spotted manner, requiring complicated scanning control of the laser beam.

On the other hand, in the case of inspection by the use of the microscope, it is possible to widen the inspection range. However, a lot of light sources have to be used for irradiating diffused light, which increases the size and cost of the apparatus. Further, while the peripheral end face of the semiconductor wafer projects like a mound, microscopes are short in the depth of field, so that it is impossible to bring all surface of the mound-like peripheral end face into focus. This makes it necessary to inspect the same range of area for observation many times by changing the focus of the microscope even if no shade is formed on the peripheral end face, which requires a very long inspection time period.

SUMMARY OF THE INVENTION

The present invention was developed in view of the above-described problems. It is an object of the present invention to provide an inspection apparatus which is capable of checking the surface of a sample for a flaw or the like with accuracy in a reduced inspection time period.

In order to achieve the object, the invention provides an inspection apparatus comprising: a diffused light source for emitting diffused light; an illuminating means for illuminating at least part of a sample with the difused light from the diffused light source, the illuminating means including a wall member defining an illuminating chamber within the wall member, the wall member having an inner wall surface for reflecting the diffused light from the diffused light source, a sample-inserting opening formed through the wall member for inserting the at least part of the sample into the illuminating chamber therethrough, and a sample-observing opening formed through the wall member for permitting light reflected from the at least part of the sample to be emitted out of the illuminating chamber; and an observing means for observing the at least part of the sample based on the light emitted via the sample-observing opening formed through the wall member of the illuminating means, the observing means including an object-side telecentric optical block having a lens system for collecting parallel light out of the light emitted via the sample-observing opening of the illuminating means, and an aperture stop disposed at or in the vicinity of a back focal point of the lens system.

According to the inspection apparatus of the invention, the inner wall of the illuminating chamber reflects the diffused light from the diffused light source repeatedly such that rays of diffused light from the diffused light source entering respective portions of the inner wall surface are reflected therefrom, and the resulting reflected rays of light are further reflected from respective opposed portions of the inner wall surface. Consequently, within the illuminating chamber, rays of light are irradiated in all directions. On the other hand, when a sample, e.g. a semiconductor wafer, is inserted through the sample-inserting opening into the illuminating chamber, the surface of the inserted portion of the sample is illuminated with rays of light from all directions. Therefore, when a peripheral end face of the semiconductor wafer is inspected, for example, no shade is formed on the peripheral end face. When the sample in this state is observed via the sample-observing block by the use of the object-side telecentric optical block, it is possible to observe a wide range of area of the sample in focus at a time since the telecentric optical system is large in the depth of field. If there is a flaw on the peripheral end face of the sample, rays of light having entered the flaw are absorbed within the flaw or reflected therefrom in various directions. When the parallel light alone is observed by reducing the degree of opening of the aperture stop of the telecentric optical block, the flaw or the like appears darker than the other portion or background of the inspected range of the peripheral end face. This makes it possible to detect the flaw in a reliable manner. Since a wide range of area of the surface can be inspected at a time, it is possible to largely reduce the inspection time period.

In one preferred embodiment of the invention, the diffused light source is arranged within the illuminating chamber of the illuminating means.

In another preferred embodiment of the invention, the diffused light source is arranged outside the illuminating means, and the illuminating means has at least one entrance opening formed through the wall member for introducing the diffused light into the illuminating chamber.

Preferably, the inspection apparatus includes sample-moving means for moving the sample in a direction perpendicular to an optical axis of the object-side telecentric optical block.

The surface of the portion of the sample within the illuminating chamber is illuminated with rays of light directly irradiated thereon from the light source as well as rays of light reflected from the inner wall surface, and this can cause a slight variation in brightness. According to this preferred embodiment, however, it is possible to reduce the variation in brightness by moving the sample in a direction perpendicular to the optical axis of the object-side telecentric optical block to thereby reduce the ratio of a quantity of directly-irradiated light on the end face of the sample to a quantity of light irradiated thereon after reflection. In this state of the peripheral end face of the sample, it is possible to distinguish a dark area caused by a flaw from such mere variation in brightness, which ensures even more reliable inspection. Further, in some cases, the moving of the sample can bring the sample to such a position as will cause directions of rays of light reflected from a flaw or the like, if any, to be so changed that almost none of reflected rays of light become parallel to the optical axis of the telecentric optical block. In this state, rays of light reflected from the flaw or the like are almost entirely cut off by the telecentric optical block, which causes a portion of the image corresponding to the flaw to be made even darker against the background. As a result, the flaw and the like can be detected with even more accuracy.

Preferably, the inspection apparatus includes rotating means for rotating the sample on an imaginary plane parallel to an imaginary plane containing the optical axis of the object-side telecentric optical block.

According to this preferred embodiment, by rotating the sample, e.g. a semiconductor wafer, it is possible to observe successive portions of the end face of the sample in a continuous manner, thereby completing inspection of the end face in a short time period.

Preferably, the wall member comprises a pair of mirror members arranged such that concave mirror surfaces thereof face toward each other, and a peripheral member being interposed between the pair of mirror members, with the sample-inserting opening and the sample-observing opening formed through respective opposite portions of the peripheral member.

Preferably, the at least one entrance opening are formed through the pair of mirror members, respectively.

For example, the pair of mirror members are each formed by an ellipsoidal mirror.

BRIEF DESCRIPTION OF THE DRAWINGS

The present invention will become more fully understood from the detailed description given hereinbelow and the accompanying drawings which are given by the way of illustration only, and thus do not limit the present invention, and wherein.

DESCRIPTION OF THE PREFERRED EMBODIMENT

The invention will now be described in detail with reference to the drawings showing embodiments thereof.

Figure 1:
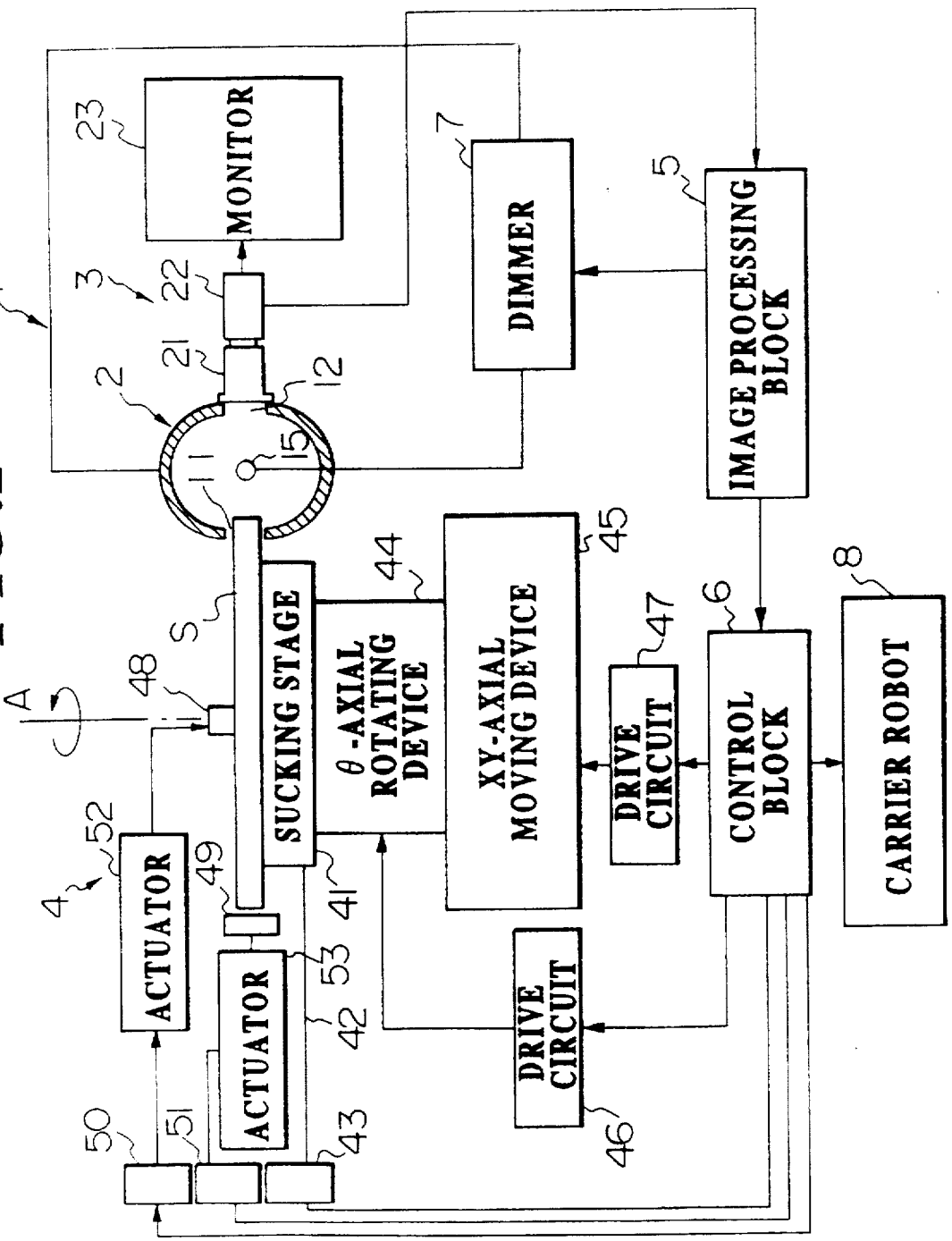
FIG. 1 is a block diagram showing the arrangement of an inspection apparatus according to a first embodiment of the invention.

Referring first to FIG. 1, there is shown an inspection apparatus 1, which is comprised of an illuminating chamber 2, an observing block 3, a sample support block 4, an image processing block 5, a control block 6, a dimmer 7, and a carrier robot 8 serving as a sample-moving means for moving the sample in a direction perpendicular to an optical axis of the object-side telecentric optical block.

The inspection apparatus 1 checks the surface of a sample S, such as a semiconductor wafer, a liquid crystal panel and a memory disk, particularly a peripheral end face of the sample S, for a flaw, a stain, a mark, a crack, etc. Now, the operation of the inspection apparatus 1 will be briefly described. Under the control of the control block 6, the carrier robot 8 places the sample S on a sucking stage 41 of the sample support block 4, and then the sucking stage 41 is moved to insert a portion of the peripheral end of the sample S into the illuminating chamber 2. In this state, the portion of the sample S inserted into the chamber 2 is uniformly illuminated with light, so that rays of light reflected from a peripheral end face of the inserted portion of the sample S enters a telecentric optical block 21 of the observing block. Then, an image of the inserted portion of the sample S is formed from light collected by the telecentric optical block 21 based on the rays of light is picked up by a CCD camera 22 of the observing block 3. The image is displayed on a monitor 23 for inspection. The condition of the peripheral end face of the sample S can be accurately observed by the above method.

Further, an image signal indicative of the image picked up by the CCD camera 22 of the observing block 3 is processed by the image processing block 5, and processed image data is delivered to the control block 6. The control block 6 automatically inspects the sample S based on the processed image data, and at the same time supplies a rotation control signal to the sample support block 4 to cause the rotation of the sample S, thereby eventually checking the whole area of the peripheral end face of the sample S. After inspection, under the control of the control block 6, the carrier block 8 replaces the sample S having been checked with a new sample S, and the above steps are repeatedly carried out thereafter.

Next, the arrangement of the inspection apparatus according to the first embodiment will be described in detail.

Figure 2:
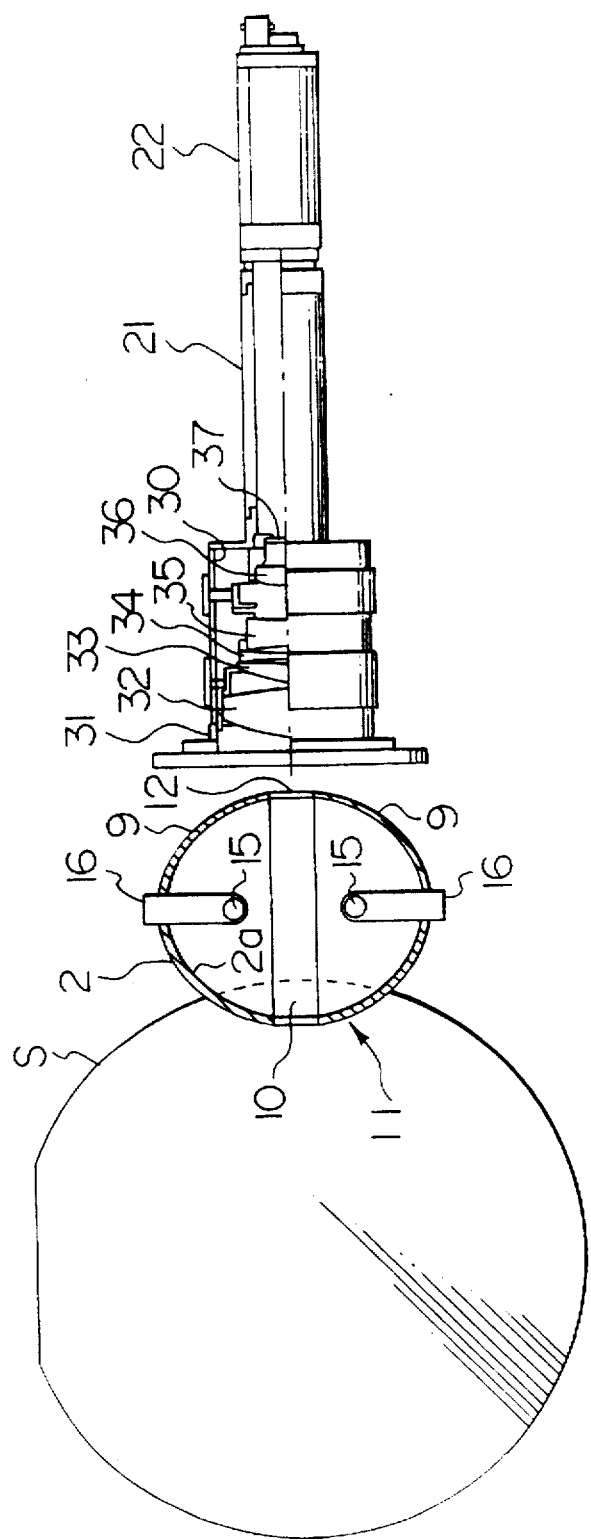
FIG. 2 is a horizontal sectional view of an illuminating chamber and an observing block appearing in FIG. 1.
Figure 3:
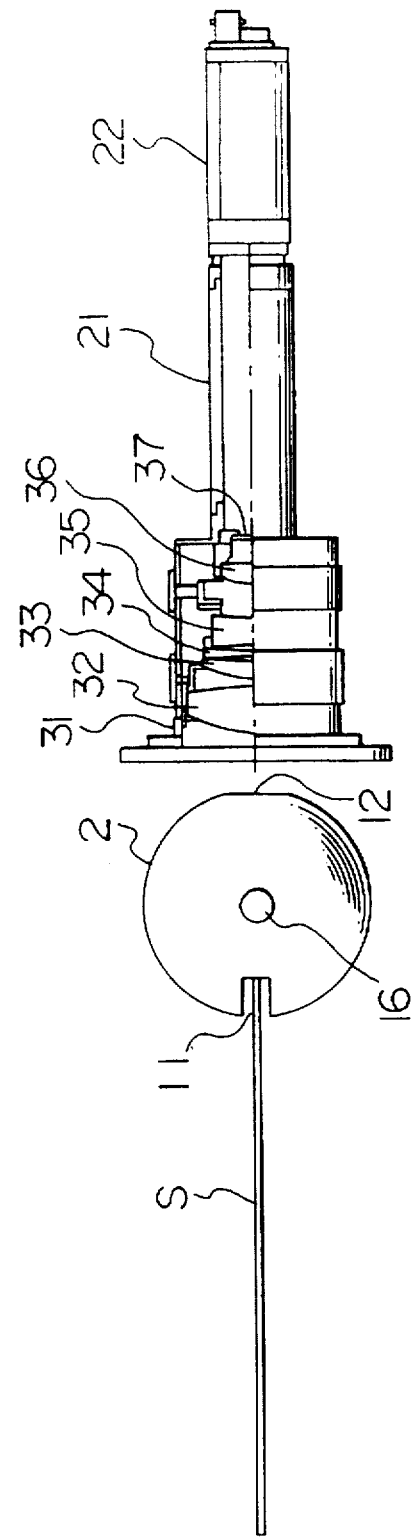
FIG. 3 is a vertical sectional view of the illuminating chamber and the observing block.

Referring to FIG. 2, the illuminating chamber 2 is defined within an assembly of two ellipsoidal mirrors 9 and 9 with concave mirror sides thereof facing toward each other and a peripheral wall 10, which is interposed between the ellipsoidal mirrors 9 and 9. The illuminating chamber 2 is thus hollow inside, and the whole inner surface 2a thereof including an inner surface of the peripheral wall 10 forms a reflecting wall for specularly reflecting light. Alternatively, the inner wall surface 2a may be coated with white diffusing paint to thereby reflect light irregularly. The illuminating chamber 2 has a sample-inserting slot 11 formed at a side (left side as viewed in FIG. 2) via which part of the peripheral end of the sample S is inserted into the illuminating chamber 2, and a sample-observing slot 12 formed at an opposite side (right side as viewed in FIG. 2) for observing light reflected from the peripheral end face of the portion of the sample S inserted into the illuminating chamber 2.

In the illuminating chamber 2 are arranged two light sources (diffused light sources) 15 for each emitting diffused light for illuminating the samples. As shown in FIG. 2, the light sources 15 are supported by light source support members 16 and 16 for disposing them at respective inner focal points of the ellipsoidal mirrors 9 and 9 the surfaces of which form, as mentioned above, part of the inner wall surface 2a. According to this arrangement, within the illuminating chamber 2, rays of light emitted from the light sources 5 are specularly reflected from the inner wall surface 2a, and portions of the inner wall surface 2a opposite to each other further reflect rays of light received from opposite ones, thus rays of the diffused light repeatedly undergoing reflection from the inner wall surface 2a. This causes rays of light to be irradiated from all directions within the illuminating chamber 2. In the present embodiment, the light sources 15 are each formed by a fluorescent discharge tube which emits a green light having a central frequency of about 530 nm, to which the CCD camera 22 is most sensitive. However, this is not limitative, but the light sources 15 may be formed by any suitable light source which emits visible light, such as a tungsten lamp, a halogen lamp, a xenon lamp, and an LED. It is preferred that the light source 15 is formed by one which emits light in a range of directions as wide as possible, i.e. a so-called diffused light source. When the LED is employed, for example, an LED chip should be singly used without a resin mold, thereby causing the same to emit diffused light. Further, in addition to the light sources provided within the illuminating chamber 2, a light source may be arranged outside the illuminating chamber 2 to collect light therefrom into an optical fiber which has an emitting end with a large angular aperture disposed within the illuminating chamber 2 for allowing the collected light to be emitted therefrom toward the inner wall surface 2a.

As shown in FIG. 1 and FIG. 2, the observing block 3 is comprised of the telecentric optical block 21 for collecting parallel light emitted from the sample-observing slot 12, the CCD camera 22 for picking up an image formed by the light collected by the telecentric optical block 21, and the monitor 23. As shown in FIG. 2, the telecentric optical block 21 is comprised of a lens barrel 31 having an inner wall 30 coated with black paint for prevention of irregular reflection, five lenses 32 to 36 disposed within the lens barrel 31 in the mentioned order, forming a telecentric lens system as a whole, and an aperture stop 37 disposed at a back focal point of the whole lens system 32 to 36. The aperture stop 37 cuts off or blocks unnecessary rays of light, such as scattered light from the surface of a peripheral end face of the sample S and noise components, to thereby collect only parallel rays of light of all the rays reflected from the sample S. Further, the depth of field of the telecentric optical block 21 is increased by reducing the degree of opening of the aperture stop 37, thereby enabling the CCD camera 22 to pick up a more tightly focused image of the sample S. The CCD camera 22 has 380 thousand pixels and delivers an image signal indicative of the image picked up thereby to the monitor 23. The monitor 23 displays an image of the peripheral end face of the sample S based on the image signal from the CCD camera 22.

As shown in FIG. 1, the sample support block 4 includes the sucking stage 41 for placing the sample S thereon. The sucking stage 41 is connected to an air compressor, not shown, via an air tube 4 and an electromagnetic valve 43 arranged therein. As the electromagnetic valve 43 is opened and closed under the control of the control block 6, the sample S placed on the sucking stage 41 is sucked to be fixed in position. Under the sucking stage 41 are arranged a θ-axial rotating device 44 and an XY-axial moving device 45. The θ-axial rotating device 44 rotates the sucking stage 41 in the direction of an arrow A in FIG. 1 in response to a rotation control signal delivered from the control block 6 via a drive circuit 46. The XY-axial moving device 45 moves the sucking stage 41 in response to a horizontal motion control signal delivered via a drive circuit 47 from the control block 6 in a direction parallel to the surface of the sheet (in the direction of X axis) and in a direction vertical to the surface of the sheet (in the direction of Y axis).

Positioning pins 48 and 49 are arranged on a remote end side (as viewed in FIG. 1) of the sucking stage in the direction of Y axis and a left end side (as viewed in FIG. 1) of the same in the direction of X axis, respectively. The positioning pins 48 and 49 are fixed to respective predetermined positions by operations of actuators 52 and 53 driven by air fed via electromagnetic valves 50 and 51 under the control of the control block 6, thereby positioning the sample S when it is placed on the sucking stage 41. In this connection, once the positioning pins 48 and 49 has put the sample S in position, they are moved in respective directions away from the sample S by returning operations of the actuators 52 and 53 caused by stoppage of operations of the electromagnetic valves 50 and 51. To position the sucking stage 41 at a reference point of origin of the sample support block 4, a reference point-positioning pin may be provided to position the sample S on the sucking stage 41 after the sucking stage 41 is positioned at the reference point of origin by the use of the reference point-positioning pin. In this case, the control block 6 may deliver a horizontal motion control signal to move the sucking stage 41 from the reference point of origin in the X-axis and Y-axis directions by a distance according to the horizontal motion control signal.

The image processing block 5 amplifies the image signal from the CCD camera 22, and converts the amplified signal into digital image data, which is delivered to the control block 6. The image processing block 5 controls quantity of light emitted from the light sources 15 and 15 by delivering a light quantity control signal to the dimmer 7 such that white level voltage (voltage of a signal, which corresponds to maximum picture brightness) is within a predetermined voltage range, i.e. for prevention of saturation of white level voltage. More specifically, the image processing block 5 supplies the dimmer 7 with the light quantity control signal as 8-bit parallel data, based on which the dimmer 7 controls voltage applied to the light sources 15 and 15 to thereby control the quantity of light emitted from the light sources 15 and 15. This makes it possible to prevent the image signal level from being saturated to allow the sample S to be observed as a clear obvious image.

The control block 6, which is formed by a host computer, checks the peripheral end face of the sample S for a flaw or the like based on the image data received from the image processing block 5. The control block 6 also detects the size of each flaw and the number of detected flaws to determine whether the sample is a conforming item or nonconforming item. Further, the control block 6 detects an ID number formed on the surface Sa of each sample S, and executes checking of the semiconductor wafer manufacturing process and various statistics processing, based on the detected ID number. During checking of the sample S, the control block 6 delivers the rotation control signal and the horizontal motion control signal to the drive circuits 46, 47 for control of rotation and horizontal motion of the sucking stage 41. On the other hand, if inspection is completed, the control block 6 delivers a control signal to the carrier robot 8 to move the sample S to a location for the next step of the manufacturing process.

The dimmer 7 changes the voltage of the power supply to the light sources 15 and 15 based on the light quantity control signal from the image processing block 5 to thereby control the quantity of light emitted from the light sources 15 and 15.

The carrier robot 8 takes a sample S out of a sample cassette carried by a conveyor belt, not shown, in response to a sample take-out signal from the control block 6, and places the taken-out sample on the sucking stage 41. After inspection of the sample S, in response to a sample return signal from the control block 6, the carrier robot 6 returns the sample S from the sucking stage 41 to the sample cassette.

Next, operation of the inspection apparatus 1 will be described.

The control block 6 causes the carrier robot 8 to place a sample S taken out of the sample cassette on the sucking stage. In this state, the sample S abuts on the positioning pins 49 and 48 to be put in position. Then, the control block 6 controls the operation of the electromagnetic valves 50 and 51 to move the positioning pins 48 and 49 to permit the sample S to rotate and move. Then, the control block 6 delivers the horizontal motion control signal to the drive circuit 47 to move the sample S to the illuminating chamber 2 to insert a portion of the sample S into the illuminating chamber 2 via the sample-inserting slot 11.

On the other hand, in the illuminating chamber 2, rays of the diffused light are reflected from the inner wall surface 2a repeatedly. That is, rays of diffused light having entered two inner wall surfaces of the two ellipsoidal mirrors 9 and 9 reflect therefrom and reflected rays of diffused light enter opposite ones of the two inner wall surfaces, thus repeatedly undergoing reflection process, so that within the illuminating chamber, rays of diffused light are irradiated in all directions. Therefore, the surfaces of inserted portion of the sample S are illuminated with rays of light from all directions, with no shade being formed on the peripheral end face of the sample S. In this state of the sample S, an image picked up by the CCD camera 22 based on light transmitted through the sample-observing slot 11 and the telecentric optical block 21 is observed on the monitor 23. Since the telecentric optical block 21 is large in the depth of field, the whole peripheral end face of the inserted portion of the sample S which is in the field of view is in focus, and no shade is formed or projected in the field of view, which enables a flaw or the like to be detected in a reliable manner.

If there is a flaw in the peripheral end face of the inserted portion of the sample S, light having entered the flaw is absorbed within the flaw or reflected therefrom in a scattered manner. Rays of light resulting from irregular reflection from the flaw, which are not parallel to the optical axis of the telecentric optical block 21, are cut off by reducing the degree of opening of the aperture stop 37 of the telecentric optical block 21, so that most rays of light reflected from the flaw are not collected, whereby an image of the peripheral end face of the sample S is formed which has a darker area against the other part or background of the image, which corresponds to the flaw in the peripheral end face of the inserted portion of the sample S. Further, since a wide rage of area can be observed at a time, the inspection time period can be largely reduced. In this connection, the control block 6 may be constructed such that it executes automatic inspection of the surface of the sample S for the flaw or the like based on the image data output from the image processing block 5.

The surfaces of the inserted portion of the sample S within the illuminating chamber 2 are illuminated with light directly irradiated thereon from the light sources 15 and 15 as well as light reflected from the inner wall surface 2a, so that there can occur a slight variation in brightness due to different kinds of illumination. To eliminate such inconvenience, the control block 6 delivers the horizontal motion control signal to the XY-axial moving device 45 via the drive circuit 47, whereby the sucking stage 41 is moved in one or both directions along the X axis and the Y axis. This can reduce the ratio of directly-irradiated light on the peripheral end face of the sample S to light irradiated thereon by reflection, to thereby reduce the variation in brightness. In this state of the peripheral end face of the samples, it is possible to distinguish a dark area or dark areas caused by a flaw or flaws from such mere variation in brightness, ensuring even more reliable inspection. Further, in some cases, the sample S can be brought to such a position as will cause directions of rays of light reflected from a flaw or the like, if any, to be so changed that almost none of reflected rays of light are parallel to the optical axis of the telecentric optical block 21. In this state, rays of light reflected from the flaw or the like are almost entirely cut off by the telecentric optical block 21, forming an even darker area against the background of the image, which corresponds to the flaw. As a result, the flaw or the like can be detected with even more accuracy.

Then, the control block 6 supplies the θ-axial rotating device 44 with the rotation control signal via the drive circuit 46, whereby the sample S is rotated. After each step of rotation, checking of a peripheral end face of an inserted portion of the sample S is carried out to complete inspection of the whole area of the peripheral end face of the sample S. After inspection, the control block 6 supplies the XY-axial moving device 45 with the horizontal motion control signal via the drive circuit 47 to move the sucking stage, thereby removing the sample S from the illuminating chamber 2. Then, the carrier robot 8 returns the sample S in the sample cassette under the control of the control block 6.

As described above, according to the first embodiment of the invention, rays of diffused light entering the inner wall surfaces of the two ellipsoidal mirrors 9 and 9 are reflected therefrom, and reflected rays of light enter opposite ones of the inner wall surfaces of the mirrors 9 and 9, to be reflected therefrom, whereby rays of light are repeatedly undergoing reflection process, so that within the illuminating chamber 2, rays of light are irradiated in all directions. This causes a portion of the sample S inserted into the illuminating chamber 2 to be illuminated with rays of light from all directions forming no shade on the peripheral end face of the sample S. As a result, when the peripheral end face of the sample S is observed by the monitor 23 by way of the telecentric optical block 21 which is large in the depth of field, the whole area of the peripheral end face of the sample S can be brought into focus, and at the same time no shade is formed in the field of view, so that it is possible to detect a flaw or the like in a reliable manner. Further, rays of light resulting from irregular reflection from the flaw are cut off by reducing the degree of opening of the aperture stop 37 of the telecentric optical block 21, whereby an image of the peripheral end face of the sample S is formed which has a darker area against the other part or background of the image, which corresponds to the flaw. Still further, since a wide rage of area can be observed at a time, the inspection time period can be largely reduced.

Next, a second embodiment of the invention will be described with reference to FIG. 4.

The second embodiment is distinguished from the first embodiment in that the light sources 15 are arranged outside the illuminating chamber 2. Therefore, component elements and parts identical to those of the first embodiment are designated by identical reference numerals, and detailed description thereof is omitted.

Figure 4:
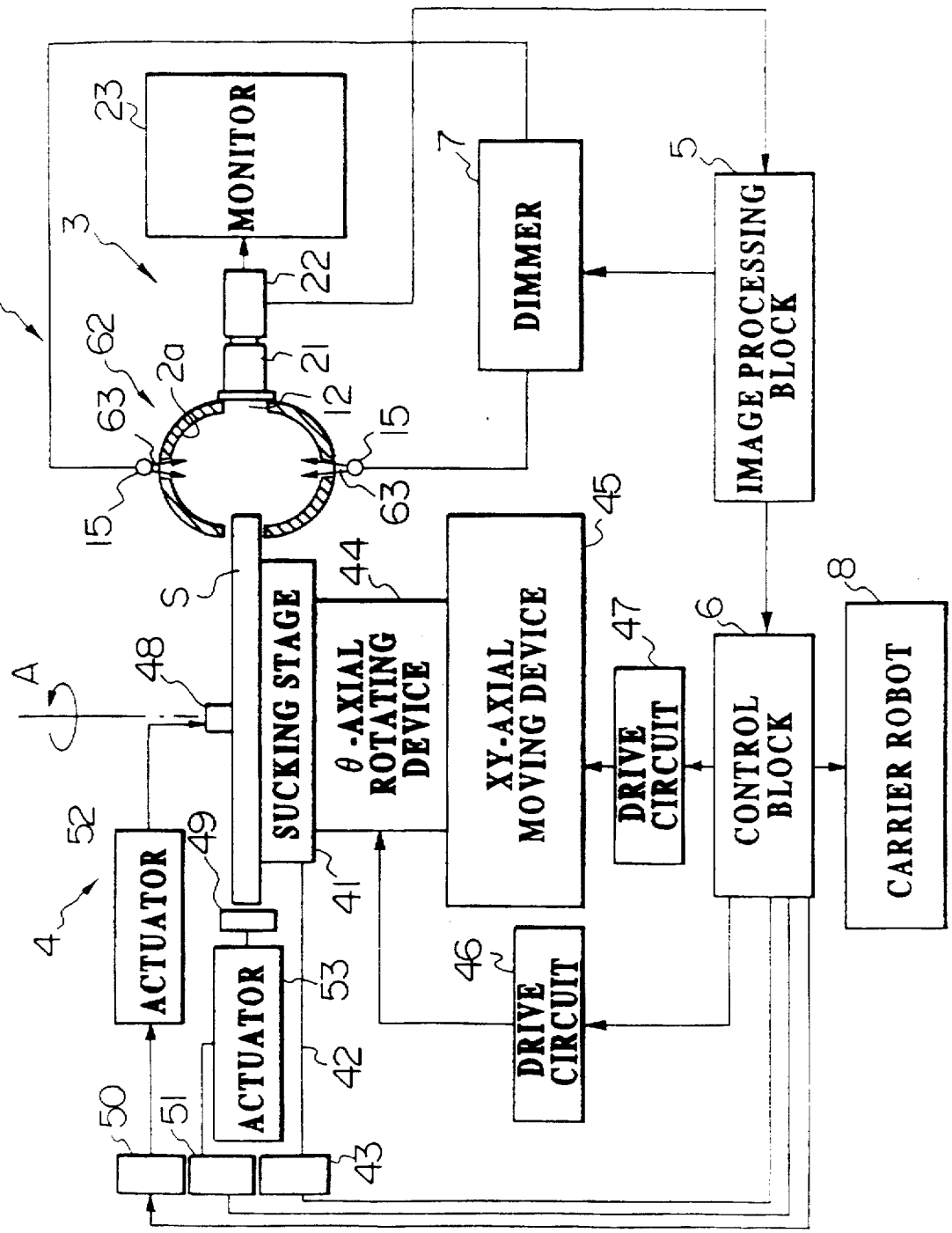
FIG. 4 is a block diagram showing the arrangement of an inspection apparatus according to a second embodiment of the invention.

As shown in FIG. 4, an inspection apparatus 61 according to the second embodiment includes two light sources 15 and 15 arranged outside an illuminating chamber 62. The illuminating chamber 62 has a construction which is substantially identical to that of the illuminating chamber 2 of the first embodiment except that light entrance ports 63 and 63 are formed through top portions of the ellipsoidal mirrors 9 and 9, respectively, for allowing the diffused light from the light sources 15 and 15 to enter the inside of the illuminating chamber 62. The light entrance ports 63 and 63 are each formed by frosted glass, which permit the diffused light from the light sources 15 and 15 to be transmitted therethrough, and at the same time cause the diffused light to enter the inside of the illuminating chamber in an even more diffused manner, thereby reducing the intensity of rays of light directly irradiated on the sample S.

According to the second embodiment, rays of diffused light having entered via the light entrance ports 63 and 63 are specularly reflected from the inner wall surfaces of the two ellipsoidal mirrors 9 and 9, and reflected rays of light enter opposite ones of the inner wall surfaces of the mirrors 9 and 9, to be reflected therefrom, whereby rays of diffused light are repeatedly undergoing reflection process, so that within the illuminating chamber 2, rays of diffused light are being irradiated or traveling in all directions. Accordingly, no shade is formed on the end face of the sample S, which makes it possible to detect the flaw or the like in a reliable manner, and a wide range of area can be observed at a time, which makes it possible to largely reduce the inspection time period.

While the invention has been described in its preferred embodiments, it is to be understood that the invention is not limited thereto, and that various changes and modifications may be made without departing from the spirit and scope thereof.

For example, although in the above embodiments, the illuminating chambers 2 and 62 are each formed by the use of a pair of ellipsoidal mirrors 9 and 9, this is not limitative, but they may be formed by any curved surface mirrors, including spherical mirrors, and non-spherical mirrors, such as parabolic reflectors. Further, the illuminating chamber may be constructed in the form of a rectangular parallelepiped or a cube with inner hollow space, with the inner wall being covered with reflection mirrors.

Further, the object-side telecentric optical block of the invention is not limited in its construction to that described with reference to the above embodiments, but may be formed by any suitable number of lens, as desired.

Further, the XY-axial moving device 45 may be constructed such that it can move in a Z-axis (upward or downward as viewed in FIG. 1) as well. Further, the light sources within the illuminating chamber 15 may be constructed such that they can be moved, which also makes it possible to check the sample S for a flaw and the like.

Further, although in the above embodiments, description is mainly made of a case in which the peripheral end face of the sample S is inspected, this is not limitative, but it goes without saying the upper or lower surface of the sample S may be inspected by the use of the inspection apparatus according to the invention. In this connection, to inspect the upper or lower surface of a semiconductor wafer or a like sample, it is only necessary to provide a sample-observing slot which extends through a portion of the wall of the illuminating chamber which faces part of the upper or lower surface of the sample in a perpendicular direction.

Further, although in the above embodiments, the inspecting observation is made by the use of the CCD camera 22, this is not limitative, but it may be effected by way of a screen on which the image is formed or directly with the eye. Further, the CCD camera may be replaced by any suitable image pick-up device including a photomultiplier.

Further, the image processing block 5 may differentiate an original picture signal contained in the signal received from the CCD camera 22 to obtain a differential signal, and then add the differential signal to the original picture signal to amplify a low contrast in the original picture signal for display on the monitor 23. Further, there may be provided a brightness adjusting circuit for adjusting the brightness level of the picture signal resulting from the addition, as desired. The brightness adjustment enables a picture or image to be observed with the optimum brightness when a peripheral end face of a sample S or an upper or lower surface of a wafer is to be observed.

What is claimed is:

1. An optical inspection apparatus, comprising
   a diffused light source;
   an illuminating member comprising a sample-inserting opening into which a peripheral end of a platelike sample is insertable, a sample-observing opening arranged at an opposite position to the sample-inserting opening, and an illuminating chamber configured to cover the inserted peripheral end of the sample which is provided with a reflecting wall member for reflecting lights from the diffused light source to uniformly illuminate the peripheral end of the sample from the surrounding thereof; and
   an observing member comprising an object-side telecentric optical block having a lens system arranged behind the sample-observing opening and configured to collect the reflected light from the peripheral end of the sample through the sample-observing opening, and having an aperture stop is arranged in a vicinity of a back focal point of the lens system.

2. An inspection apparatus according to claim 1, wherein said diffused light source is arranged within said illuminating chamber of said illuminating means.

3. An inspection apparatus according to claim 2, further comprising a sample-moving means for moving said sample in a direction perpendicular to an optical axis of said object-side telecentric optical block.

4. An inspection apparatus according to claim 3, further comprising a rotating means for rotating said sample on an imaginary plane parallel to an imaginary plane containing said optical axis of said object-side telecentric optical block.

5. An inspection apparatus according to claim 2, wherein said wall member comprises a pair of mirror members having concave mirror surfaces which face toward each other, and a peripheral member being interposed between said pair of mirror members and having a mirror surface inside, with said sample-inserting opening and said sample-observing opening formed through respective opposite portions of said peripheral member.

6. An inspection apparatus according to claim 5, wherein each of said pair of mirror members forms an ellipsoidal mirror.

7. An inspection apparatus according to claim 1, wherein said diffused light source is arranged outside said illuminating member which has at least one entrance opening formed through said wall member for introducing said diffused light into said illuminating chamber.

8. An inspection apparatus according to claim 7, further comprising a sample-moving means for moving said sample in a direction perpendicular to an optical axis of said object-side telecentric optical block.

9. An inspection apparatus according to claim 8, further comprising a rotating means for rotating said sample on an imaginary plane parallel to an imaginary plane containing said optical axis of said object-side telecentric optical block.

10. An inspection apparatus according to claim 7, wherein said wall member comprises a pair of mirror members having concave mirror surfaces which face toward each other, and a peripheral member being interposed between said pair of mirror members and having a mirror surface inside, with said sample-inserting opening and said sample-observing opening formed through respective opposite portions of said peripheral member.

11. An inspection apparatus according to claim 10, wherein said at least one entrance opening are formed through said pair of mirror members, respectively.

12. An inspection apparatus according to claim 10, wherein each of said pair of mirror members forms an ellipsoidal mirror.

* * * * *